(12) United States Patent
Miracle et al.

(10) Patent No.: US 7,507,700 B2
(45) Date of Patent: Mar. 24, 2009

(54) ORGANIC CATALYST WITH ENHANCED SOLUBILITY

(75) Inventors: Gregory Scot Miracle, Hamilton, OH (US); George Douglas Hiler, II, Harrison, OH (US); Susumu Murata, Shimane (JP); Rebecca Massie Grey, West Alexandria, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 242 days.

(21) Appl. No.: 11/437,098

(22) Filed: May 19, 2006

(65) Prior Publication Data

US 2006/0211590 A1  Sep. 21, 2006

Related U.S. Application Data

(63) Continuation of application No. 10/447,506, filed on May 29, 2003, now Pat. No. 7,169,744.

(60) Provisional application No. 60/386,692, filed on Jun. 6, 2002, provisional application No. 60/426,549, filed on Nov. 15, 2002.

(51) Int. Cl.
*C11D 3/00* (2006.01)
*C07D 285/00* (2006.01)

(52) U.S. Cl. .................. 510/367; 548/400; 548/959; 252/186.38

(58) Field of Classification Search .................. None
See application file for complete search history.

(56) References Cited

U.S. PATENT DOCUMENTS

| | | |
|---|---|---|
| 3,822,114 A | 7/1974 | Montgomery et al. |
| 4,001,131 A | 1/1977 | Montgomery et al. |
| 4,096,141 A | 6/1978 | Milkowski et al. |
| 4,194,987 A | 3/1980 | Brubaker |
| 4,325,957 A | 4/1982 | Zeugner et al. |
| 4,430,243 A | 2/1984 | Bragg et al. |
| 4,505,908 A | 3/1985 | Zeugner et al. |
| 4,595,531 A | 6/1986 | Milkowski et al. |
| 4,977,252 A | 12/1990 | Chiu |
| 5,041,232 A | 8/1991 | Batal et al. |
| 5,045,223 A | 9/1991 | Batal et al. |
| 5,047,163 A | 9/1991 | Batal et al. |
| 5,310,925 A | 5/1994 | Batal et al. |
| 5,354,559 A | 10/1994 | Morehouse |
| 5,360,568 A | 11/1994 | Madison et al. |
| 5,360,569 A | 11/1994 | Madison et al. |
| 5,370,826 A | 12/1994 | Madison et al. |
| 5,413,733 A | 5/1995 | Nicholson et al. |
| 5,442,066 A | 8/1995 | Madison et al. |
| 5,478,357 A | 12/1995 | Madison et al. |
| 5,482,515 A | 1/1996 | Madison et al. |
| 5,486,303 A | 1/1996 | Capeci et al. |
| 5,489,392 A | 2/1996 | Capeci et al. |
| 5,516,448 A | 5/1996 | Capeci et al. |
| 5,550,256 A | 8/1996 | Madison et al. |
| 5,565,422 A | 10/1996 | Del Grecco et al. |
| 5,569,645 A | 10/1996 | Dinniwell et al. |
| 5,574,005 A | 11/1996 | Welch et al. |
| 5,576,282 A | 11/1996 | Miracle et al. |
| 5,576,448 A | 11/1996 | Van Daele et al. |
| 5,595,967 A | 1/1997 | Miracle et al. |
| 5,597,936 A | 1/1997 | Perkins et al. |
| 5,620,969 A | 4/1997 | Bronson et al. |
| 5,652,207 A | 7/1997 | Ghatlia |
| 5,691,297 A | 11/1997 | Nassano et al. |
| 5,692,650 A | 12/1997 | Wolter et al. |
| 5,693,603 A | 12/1997 | Ghatlia |
| 5,710,116 A | 1/1998 | Miracle et al. |
| 5,753,599 A | 5/1998 | Coope et al. |
| 5,760,222 A | 6/1998 | Coope |
| 5,817,614 A | 10/1998 | Miracle et al. |
| 5,835,826 A | 11/1998 | Okada et al. |
| 5,879,584 A | 3/1999 | Bianchetti et al. |
| 5,952,282 A | 9/1999 | Löffler et al. |
| 6,007,583 A | 12/1999 | Nestler |
| 6,093,712 A | 7/2000 | Matiskella et al. |
| 6,120,557 A | 9/2000 | Nestler |
| 6,225,464 B1 | 5/2001 | Hiler, II et al. |
| 6,306,812 B1 | 10/2001 | Perkins et al. |
| 6,326,348 B1 | 12/2001 | Vinson et al. |
| 6,818,607 B1 | 11/2004 | Dykstra et al. |
| 6,821,935 B1 | 11/2004 | Dykstra et al. |
| 6,825,160 B1 | 11/2004 | Dykstra et al. |
| 6,887,838 B2 | 5/2005 | Dykstra et al. |
| 6,903,060 B1 | 6/2005 | Dykstra et al. |
| 7,109,156 B1 | 9/2006 | Dykstra et al. |
| 7,169,744 B2 | 1/2007 | Miracle et al. |
| 2002/0123445 A1 | 9/2002 | Dykstra et al. |
| 2005/0009719 A1 | 1/2005 | Dykstra et al. |
| 2005/0070454 A1 | 3/2005 | Dykstra et al. |
| 2005/0113246 A1 | 5/2005 | Hiler, II et al. |
| 2005/0256017 A1 | 11/2005 | Dykstra |
| 2006/0089284 A1 | 4/2006 | Miracle et al. |
| 2006/0252667 A1 | 11/2006 | Mort, III et al. |
| 2007/0197417 A1 | 8/2007 | Miracle et al. |

FOREIGN PATENT DOCUMENTS

CA       1122980      5/1982

(Continued)

OTHER PUBLICATIONS

W. Whaley et al., The Preparation of 3,4 Dihydroisoquinolines and Related Compounds by the Bischler-Napieralski Reaction, Organic reactions (1951), VI 74-150.
Lee et al., Tetrahedron Letters, 1996, vol. 37, No. 21, pp. 3663-3666.
Allevi et al., A Simple and Convenient Transformation if L-lysine into Pyridinoline and Deoxpyridinoline, two collagen cross-links of Biochemical Interest, Tetrahedron: Asymmetry 13, (2002) 1091-1910.

(Continued)

*Primary Examiner*—Kamal A Saeed
(74) *Attorney, Agent, or Firm*—James F. McBride; Kim William Zerby; Steven W. Miller

(57) ABSTRACT

This invention relates to organic catalysts comprising iminium or oxaziridinium moieties, cleaning compositions comprising such catalysts; and processes for making and using such catalysts and cleaning products.

4 Claims, No Drawings

FOREIGN PATENT DOCUMENTS

| | | |
|---|---|---|
| JP | 06-308655 | 11/1994 |
| WO | WO 95/13351 A1 | 5/1995 |
| WO | WO 95/13352 A1 | 5/1995 |
| WO | WO 95/13353 A1 | 5/1995 |
| WO | WO 95/28399 A1 | 10/1995 |
| WO | WO 97/06147 A1 | 2/1997 |
| WO | WO 97/10323 A1 | 3/1997 |
| WO | WO 97/11151 A1 | 3/1997 |
| WO | WO 98/07825 A2 | 2/1998 |
| WO | WO 98/15535 A1 | 4/1998 |
| WO | WO 98/16614 A1 | 4/1998 |
| WO | WO 98/23602 A1 | 6/1998 |
| WO | WO 98/23717 A2 | 6/1998 |
| WO | WO 00/32601 A2 | 6/2000 |
| WO | WO 00/42156 A1 | 7/2000 |
| WO | WO 01/16110 A1 | 3/2001 |
| WO | WO 01/16263 A2 | 3/2001 |
| WO | WO 01/16273 A1 | 3/2001 |
| WO | WO 01/16274 A1 | 3/2001 |
| WO | WO 01/16275 A1 | 3/2001 |
| WO | WO 01/16276 A1 | 3/2001 |
| WO | WO 01/16277 A1 | 3/2001 |
| WO | WO 01/16278 A1 | 3/2001 |
| WO | WO 03/104199 A2 | 12/2003 |

OTHER PUBLICATIONS

Mangalagiu et al., Diazinium Carbalkoxy Methylides, Bd. Copou, No. 11, Iasi-6600, Romania, Al, I. Cuza, University, Department of Organic Chemistry, pp. 73-79.

La Berre, Andre, "Alpha- Sulfocarboylic acids and derivatives. III. Sulfonation and Chlorosulfonation of Acrylic and 3-Chloropropionic Acids" Bulletin de la Societe Chimique de France (1973), (7-8) (Pt. 2), 2266-2269.

Abstract—Pyridinium, 1-(1-carboxy-3-cyano-4-ethoxy-4-oxo-2-butenyl)-, inner salt, Timtec Stock Library.

Mangalagiu et al., 4-Methylpyrimidinium Ylides II, Selective Reactions of Pyrimidinium Ylides with Activated Alkynes, Al, I. Cuza, University, Organic Chemistry Dept, (2000) pp. 2047-2050.

Korshin, E. E., The Reaction of Tertiary Amines With Maleic Acid and Monoalkyl Maleates, Zhurnal Obshchei Khimii, vol. 60(122), No. 5 (May 1990), pp. 1170-1175.

Zugravescu, M, Die Addition Von Philodienen an Phthalazin, Revue Roumaine de Chimi, 12, (1967) pp. 109-116.

Rucinschi, E, Dienophile Addition an Heterozyklischen Verbindungen II, Revue Roumaine deChimie, vol. 13, No. 5, (1968), pp. 637-646.

Undheim, K. Pyridium-3-Oxide Derivatives From Amino Acids, Part IX, N-Quaternary Compounds, Acta Chemica Scandinavica 23 ( 1969) pp. 2475-2487.

Undheim, K, The Menschutkin Reaction, Part XIX, N-Quaternary Compounds, Acta Chemica Scandinavica, 25, (1971) pp. 18-26.

Le Berre, A, Acides àSulfo β-Amino Carbozyliques (Taurines à-Carboyzliques), Bull Soc. Chim. FR, (1974) pp. 221-224.

Wittman, H, Reactions With Betaine, VII; Reactions of Ethyl Malonate-Enolbetaines With Phenyl Isocyanate, Monatschefte fur Chemie 102, (1971), pp. 1120-1128.

Acheson, R.M., Addition Reactions of Heterocyclic Compounds, XVII, The structures and reactions of adducts from pyridines, dimethyl acetylenedicarboxylate, and carbon dioxide at low temperatures, Univ. of Oxford, Journal of the Chemical Society, Abstracts (1964).

H. Böhme et al., *Uber Derivate des 1,2,3,4,5-Pentahydro-2-benzazepins*, Arch Pharm, vol. 306 (4), 1972, pp. 271-274.

ORGANIC CATALYST WITH ENHANCED SOLUBILITY

CROSS-REFERENCES TO RELATED APPLICATIONS

This application is a continuation of and claims priority under 35 U.S.C. § 120 to U.S. patent application Ser. No. 10/447,506, filed May 29, 2003 now U.S. Pat. No. 7,169,744, which in turn claims priority under 35 U.S.C. § 119(e) to U.S. Provisional Application Ser. No. 60/386,692 filed Jun. 6, 2002 and U.S. Provisional Application Ser. No. 60/426,549 filed Nov. 15, 2002.

FIELD OF INVENTION

This invention relates to organic catalysts and cleaning compositions comprising such catalysts; and processes for making and using such catalysts and cleaning products.

BACKGROUND OF THE INVENTION

Oxygen bleaching agents, for example hydrogen peroxide, are typically used to facilitate the removal of stains and soils from clothing and various surfaces. Unfortunately such agents are extremely temperature rate dependent. As a result, when such agents are employed in colder solutions, the bleaching action of such solutions is markedly decreased.

In an effort to resolve the aforementioned performance problem, the industry developed a class of materials known as "bleach activators". However, as such materials rapidly lose their effectiveness at solution temperatures of less than 40° C., new organic catalysts such as 3,4-dihydro-2-[2-(sulfooxy)decyl]isoquinolimium, inner salt were developed. In general, while such current art catalysts are effective in lower temperature water conditions, they can inactivate certain enzymes and the more effective catalysts tend to be hydrophobic—thus their aqueous solubility is limited. As most laundry and cleaning compositions are formulated in, or intended to be used with water, formulating cleaning products with such catalysts can be problematic.

Accordingly, there is a need for an inexpensive organic catalyst that can provide the combined benefits of formulation flexibility, and low water temperature bleaching performance.

SUMMARY OF THE INVENTION

The present invention relates to organic catalysts having enhanced solubility. The present invention also relates to cleaning compositions comprising said organic catalysts, and processes for making and using the aforementioned organic catalysts and cleaning compositions.

DETAILED DESCRIPTION OF THE INVENTION

Definitions

As used herein, the term "cleaning composition" includes, unless otherwise indicated, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the phrase "is independently selected from the group consisting of . . . " means that moieties or elements that are selected from the referenced Markush group can be the same, can be different or any mixture of elements as indicated in the following example:

A molecule having 3 R groups wherein each R group is independently selected from the group consisting of A, B and C.

Here the three R groups may be: AAA, BBB, CCC, AAB, AAC, BBA, BBC, CCA, CCB, ABC.

As used herein, "substituted" means that the organic composition or radical to which the term is applied is:

(a) made unsaturated by the elimination of elements or radical; or (b) at least one hydrogen in the compound or radical is replaced with a moiety containing one or more (i) carbon, (ii) oxygen, (iii) sulfur, (iv) nitrogen or (v) halogen atoms; or (c) both (a) and (b).

Moieties that may replace hydrogen as described in (b) immediately above, which contain only carbon and hydrogen atoms are all hydrocarbon moieties including, but not limited to, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Specific non-limiting examples of such groups are:

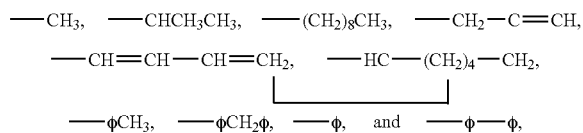

Moieties containing oxygen atoms that may replace hydrogen as described in (b) immediately above include hydroxy, acyl or keto, ether, epoxy, carboxy, and ester containing groups. Specific non-limiting examples of such oxygen containing groups are:

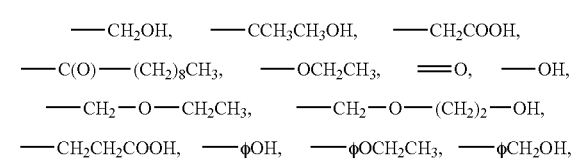

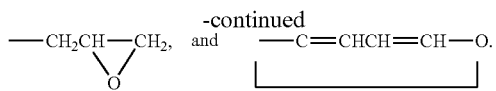

Moieties containing sulfur atoms that may replace hydrogen as described in (b) immediately above include the sulfur-containing acids and acid ester groups, thioether groups, mercapto groups and thioketo groups. Specific non-limiting examples of such sulfur containing groups are:

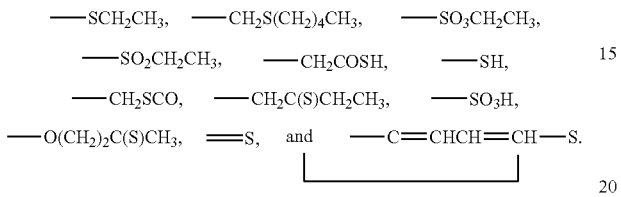

Moieties containing nitrogen atoms that may replace hydrogen as described in (b) immediately above include amino groups, the nitro group, azo groups, ammonium groups, amide groups, azido groups, isocyanate groups, cyano groups and nitrile groups. Specific non-limiting examples of such nitrogen containing groups are: —NHCH$_3$, —NH$_2$, —NH$_3^+$, —CH$_2$CONH$_2$, —CH$_2$CON$_3$, —CH$_2$CH$_2$CH=NOH, —CAN, —CH(CH$_3$)CH$_2$NCO, —CH$_2$NCO, —N$\phi$, —$\phi$N=N$\phi$OH, and ≡N.

Moieties containing halogen atoms that may replace hydrogen as described in (b) immediately above include chloro, bromo, fluoro, iodo groups and any of the moieties previously described where a hydrogen or a pendant alkyl group is substituted by a halo group to form a stable substituted moiety. Specific non-limiting examples of such halogen containing groups are: —(CH$_2$)$_3$COCl, —$\phi$F$_5$, —$\phi$Cl, —CF$_3$, and —CH$_2\phi$Br.

It is understood that any of the above moieties that may replace hydrogen as described in (b) can be substituted into each other in either a monovalent substitution or by loss of hydrogen in a polyvalent substitution to form another monovalent moiety that can replace hydrogen in the organic compound or radical.

As used herein "$\phi$" represents a phenyl ring.

All documents cited are, in relevant part, incorporated herein by reference; the citation of any document is not to be construed as an admission that it is prior art with respect to the present invention.

Organic Catalyst

In one aspect of Applicants' invention, Applicants' catalyst has Formula 1 below:

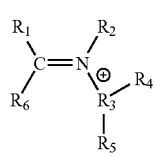

Formula I wherein:
R$_1$ is a aryl or heteroaryl group that can be substituted or unsubstituted;
R$_2$ is a substituted or unsubstituted alkyl;
R$_1$ and R$_2$ when taken together with the iminium form a ring;
R$_3$ is a C$_1$ to C$_{20}$ substituted alkyl;
R$_4$ is the moiety Q$_t$-A
  wherein: Q is a branched or unbranched alkylene
    t=0 or 1 and
    A is an anionic group selected from the group consisting
      of OSO$_3^-$, SO$_3^-$, CO$_2^-$, OCO$_2^-$, OPO$_3^{2-}$, OPO$_3$H$^-$ and
      OPO$_2^-$;
R$_5$ is the moiety —CR$_{11}$R$_{12}$—X-G$_b$-X$_c$—[(CR$_9$R$_{10}$)$_y$—O]$_k$—R$_8$
  wherein: each X is independently selected from the group
    consisting of O, S, N—H, or N—R$_8$; and
    each R$_8$ is independently selected from the group consisting of alkyl, aryl and heteroaryl, said R$_8$ moieties being substituted or unsubstituted, and whether substituted or unsubsituted said R$_8$ moieties having less than 21 carbons;
    each G is independently selected from the group consisting of CO, SO$_2$, SO, PO and PO$_2$;
    R$_9$ and R$_{10}$ are independently selected from the group consisting of H and C$_1$-C$_4$ alkyl; and
    R$_{11}$ and R$_{12}$ are independently selected from the group consisting of H and alkyl, or when taken together may join to form a carbonyl; and
    b=0 or 1;
    c can=0 or 1, but c must=0 if b=0;
    y is an integer from 1 to 6;
    k is an integer from 0 to 20; and
R$_6$ is H, or an alkyl, aryl or heteroaryl moiety; said moieties being substituted or unsubstituted.

In another aspect of Applicants' invention, Applicants' catalyst has the Formula 1 above wherein:
R$_1$ is a aryl or heteroaryl group that can be substituted or unsubstituted;
R$_2$ is a substituted or unsubstituted alkyl;
R$_1$ and R$_2$ when taken together with the iminium form a ring;
R$_3$ is a C$_1$ to C$_{12}$ substituted alkyl;
R$_4$ is the moiety Q$_t$-A
  wherein: Q is a C$_1$ to C$_3$ alkyl;
    t=0 or 1 and
    A is an anionic group selected from the group consisting of OSO$_3^-$, SO$_3^-$, CO$_2^-$, and OCO$_2^-$;
R$_5$ is the moiety —CR$_{11}$R$_{12}$—X-G$_b$-X$_c$—R$_8$
  wherein: each X is independently selected from the group consisting of O, S, N—H, or N—R$_8$; and
    each R$_8$ is independently selected from the group consisting of alkyl, aryl and heteroaryl, said R$_8$ moieties being substituted or unsubstituted, and whether substituted or unsubstituted said R$_8$ moieties having less than 21 carbons;
    each G is independently selected from the group consisting of CO, SO$_2$, SO, PO and PO$_2$;
    R$_{11}$ and R$_{12}$ are independently selected from the group consisting of H and alkyl;
    b=0 or 1;
    c can=0 or 1, but c must=0 if b=1; and $R_6$ is H, or an alkyl, aryl or heteroaryl moiety; said moieties being substituted or unsubstituted.

In another aspect of Applicants' invention, Applicants' catalyst has Formula 1 above:

wherein:
$R_1$ is a aryl or heteroaryl group that can be substituted or unsubstituted;
$R_2$ is a substituted or unsubstituted alkyl;
$R_1$ and $R_2$ when taken together with the iminium form a six membered ring;
$R_3$ is a substituted $C_2$ alkyl;
$R_4$ is $OSO_3^-$;
$R_5$ is the moiety —$CH_2$—O—$R_8$ wherein $R_8$ is independently selected from the group consisting of alkyl, aryl and heteroaryl, said $R_8$ moiety being substituted or unsubstituted, and whether substituted or unsubsituted said $R_8$ moiety having less than 21 carbons; and
$R_6$ is H, or an alkyl, aryl or heteroaryl moiety; said moieties being substituted or unsubstituted.

In another aspect of Applicants' invention, Applicants' catalyst has Formula 2 below:

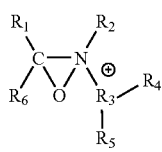

Formula 2 wherein:
$R_1$ is a aryl or heteroaryl group that can be substituted or unsubstituted;
$R_2$ is a substituted or unsubstituted alkyl;
$R_1$ and $R_2$ when taken together with the carbon and the nitrogen of the oxaziridinium form a ring;
$R_3$ is a $C_1$ to $C_{20}$ substituted alkyl;
$R_4$ is the moiety $Q_t$-A
wherein: Q is a branched or unbranched alkylene
t=0 or 1 and
A is an anionic group selected from the group consisting of $OSO_3^-$, $SO_3^-$, $CO_2^-$, $OCO_2^-$, $OPO_3^{2-}$, $OPO_3H^-$ and $OPO_2^-$;
$R_5$ is the moiety —$CR_{11}R_{12}$—X-$G_b$-$X_c$—$[(CR_9R_{10})_y$—$O]_k$—$R_8$
wherein: each X is independently selected from the group consisting of O, S, N—H, or N—$R_8$; and
each $R_8$ is independently selected from the group consisting of alkyl, aryl and heteroaryl, said $R_8$ moieties being substituted or unsubsituted, and whether substituted or unsubsituted said $R_8$ moieties having less than 21 carbons;
each G is independently selected from the group consisting of CO, $SO_2$, SO, PO and $PO_2$;
$R_9$ and $R_{10}$ are independently selected from the group consisting of H and $C_1$-$C_4$ alkyl; and
$R_{11}$ and $R_{12}$ are independently selected from the group consisting of H and alkyl, or when taken together may form a carbonyl;
b=0 or 1;
c can=0 or 1, but c must=0 if b=0;
y is an integer from 1 to 6;
k is an integer from 0 to 20; and
$R_6$ is H, or an alkyl, aryl or heteroaryl moiety; said moieties being substituted or unsubstituted.

In another aspect of Applicants' invention, Applicants' catalyst has the Formula 2 above:

wherein:
$R_1$ is a aryl or heteroaryl group that can be substituted or unsubstituted;
$R_2$ is a substituted or unsubstituted alkyl;
$R_1$ and $R_2$ when taken together with the carbon and the nitrogen of the oxaziridinium form a ring;
$R_3$ is a $C_1$ to $C_{12}$ substituted alkyl;
$R_4$ is the moiety $Q_t$-A
wherein: Q is a $C_1$ to $C_3$ alkyl;
t=0 or 1 and
A is an anionic group selected from the group consisting of $OSO_3^-$, $SO_3^-$, $CO_2^-$, and $OCO_2^-$;
$R_5$ is the moiety —$CR_{11}R_{12}$—X-$G_b$-$X_c$—$R_8$
wherein: each X is independently selected from the group consisting of O, S, N—H, or N—$R_8$; and
each $R_8$ is independently selected from the group consisting of alkyl, aryl and heteroaryl, said $R_8$ moieties being substituted or unsubstituted, and whether substituted or unsubsituted said $R_8$ moieties having less than 21 carbons;
each G is independently selected from the group consisting of CO, $SO_2$, SO, PO and $PO_2$;
$R_{11}$ and $R_{12}$ are independently selected from the group consisting of H and alkyl;
b=0 or 1;
c can=0 or 1, but c must=0 if b=1; and
$R_6$ is H, or an alkyl, aryl or heteroaryl moiety; said moieties being substituted or unsubstituted.

In another aspect of Applicants' invention, Applicants' catalyst has Formula 2 above:

wherein:
$R_1$ is a aryl or heteroaryl group that can be substituted or unsubstituted;
$R_2$ is a substituted or unsubstituted alkyl;
$R_1$ and $R_2$ when taken together with the carbon and the nitrogen of the oxaziridinium form a six member ring;
$R_3$ is a substituted $C_2$ alkyl;
$R_4$ is $OSO_3^-$;
$R_5$ is the moiety —$CH_2$—O—$R_8$ wherein $R_8$ is independently selected from the group consisting of alkyl, aryl and heteroaryl, said $R_8$ moiety being substituted or unsubstituted, and whether substituted or unsubsituted said $R_8$ moiety having less than 21 carbons; and
$R_6$ is H, or an alkyl, aryl or heteroaryl moiety; said moieties being substituted or unsubstituted.

Applicants have found that judicious selection of the $R_5$ moiety for the organic catalyst embodiments of the present invention provides the requisite enhanced solubility necessary to obtain the combined benefits of formulation flexibility, and low water temperature bleaching performance. While not being bound by theory, Applicants believe this is due to the dipole-enhancing and, optionally, crystallinity-inhibiting properties of said $R_5$ moieties.

Processes of Making Organic Catalysts

Suitable routes for preparing Applicants' organic catalysts include, but are not limited to, the synthetic routes detailed below:

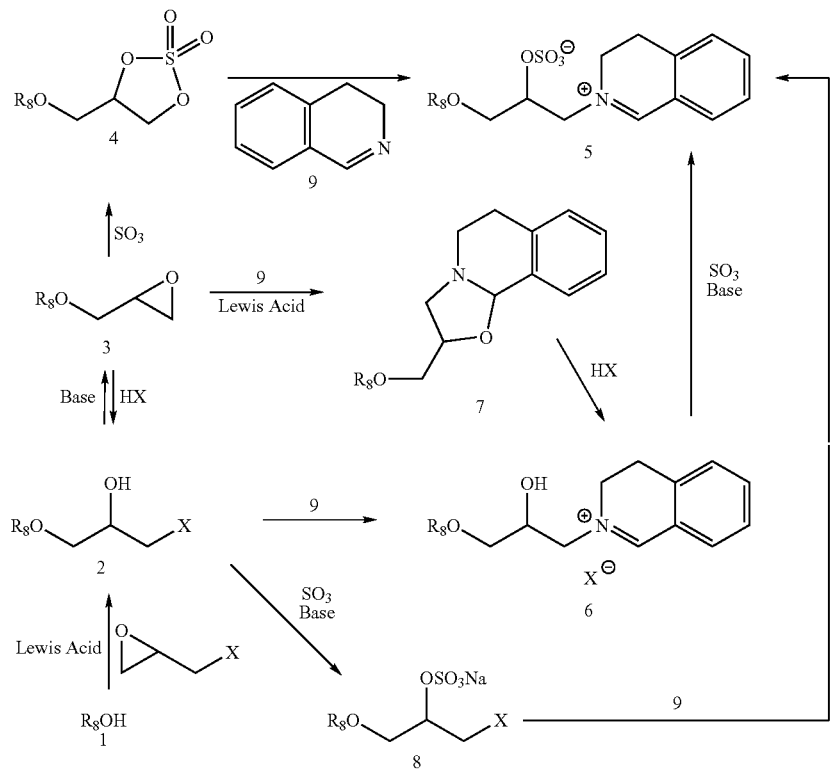

Alcohol 1 may be converted to halohydrin 2 via Lewis acid catalyzed addition to epihalohydrin, followed by (a) base induced ring closure to epoxide 3 and subsequent ring opening with HX, or (b) halogen exchange reaction. Halohydrin 2 may be converted to product 5 by (1) alkylating dihydroisoquinoline 9 and then sulfating (2 to 6 to 5), or (2) sulfating and then alkylating 9 (2 to 8 to 5). Alternatively, the product may be obtained from epoxide 3 via (1) conversion to cyclic sulfate 4 and reaction with dihydroisoquinoline 9, or (2) Lewis acid catalyzed addition to 9 to form oxazolidine 7 which is opened under acidic conditions to 6 and subsequently sulfated. While the synthetic pathways detailed above employ specifically substituted reagents, as will be appreciated by one skilled in the art, reagents with different substituents may be employed if other products are desired.

Raw materials required for the aforementioned syntheses are generally commercial available. For example, glycidal ethers such as (2-ethylhexyloxy)oxiran-2-ylmethane can be acquired through the Raschig Corporation, 129 South Scoville Avenue, Oak Park Ill., 60302, U.S.A, under the product name EHGE. 3,4-Dihydroisoquinoline can be prepared by the Bischler-Napieralski reaction, as described by Whaley et al (W. Whaley et al, *Organic reactions* (1951), VI 74-150). Halohydrins, such as 1-Bromo-3-(2-ethyl-hexyloxy)-propan-2-ol and cyclic sulfates such as 4-[(2-ethylhexyloxymethyl]-1,3,2-dioxathiolane-2,2-dione can be prepared by the detailed procedures described in Applicants Examples.

The synthesis paths that Applicants' developed allow commercial quantities of cyclic sulfate to be produced using falling film reactors wherein cyclic sulfate is produced by the process of: 1.) introducing the appropriate glycidal ether into a dry stream of $SO_3$ gas, 2.) contacting said reagents within the falling film reactor, 3.) then optionally holding the resulting reaction mixture at a sufficient temperature for a sufficient time to achieve the desired conversion, and 4.) optionally isolating the resulting cyclic sulfate. As appreciated by the skilled artisan, reaction conditions vary depending on equipment type. However, when in possession of the teachings contained herein, such conditions are easily determined.

Commercial quantities of Applicants' catalyst can be produced using a variety of reaction vessels and processes including batch, semi-batch and continuous processes. Non-limiting procedures for producing Applicants catalyst include contacting glycidal ether with an $SO_3$ complex, either neat or with an appropriate aprotic solvent for less than about 60 minutes, at a temperature of from about 75° C. to about 130° C., and a pressure of about 1 atmosphere to form the desired cyclic sulfate. Final conversion to the desired organic catalyst is achieved by contacting the cyclic sulfate with a 3,4-dihydroisoquinoline for less than about 24 hours, at a temperature of from about 20° C. to about 50° C., and a pressure of about 1 atmosphere.

In addition to the procedure described above, Applicants' catalyst can be produced by first producing a halohydrin, such as 1-bromohydrin, by contacting a glycidal ether with hydrobromic acid for less than about 10 minutes, at a temperature of from about 0° C. to about 40° C., and a pressure of about 1 atmosphere, and then isolating the 1-bromohydrin through conventional means that include but are not limited to extraction and distillation. Next the 1-bromohydrin is reacted with a 3,4-dihydroisoquinoline for about 48 hours, at a temperature of about 40° C. and a pressure of about 1 atmosphere to form alcohol salt which is subsequently sulfated in the same reaction vessel via a sulfating agent such as $SO_3$, an $SO_3$ complex, $HSO_3Cl$ or mixture thereof to generate the desired product.

The oxaziridinium ring containing version of Applicants' catalyst may be produced by contacting an iminium ring containing version of Applicants' catalysts with an oxygen transfer agent such as a peroxycarboxylic acid. Such species can be formed in situ and used without purification.

Cleaning Compositions and Cleaning Composition Additives Comprising Applicants' Organic Catalysts The cleaning composition of the present invention may be advantageously employed for example, in laundry applications, hard surface cleaning, automatic dishwashing applications, as well as cosmetic applications such as dentures, teeth, hair and skin. However, due to the unique advantages of both increased effectiveness in lower temperature solutions and the superior color-safety profile, the organic catalysts of the present invention are ideally suited for laundry applications such as the bleaching of fabrics through the use of bleach containing detergents or laundry bleach additives. Furthermore, the organic catalysts of the present invention may be employed in both granular and liquid compositions.

The organic catalysts of the present invention may also be employed in a cleaning additive product. A cleaning additive product including the organic catalysts of the present invention is ideally suited for inclusion in a wash process when additional bleaching effectiveness is desired. Such instances may include, but are not limited to, low temperature solution cleaning application. The additive product may be, in its simplest form, Applicants' organic catalyst. Preferably, the additive could be packaged in dosage form for addition to a cleaning process where a source of peroxygen is employed and increased bleaching effectiveness is desired. Such single dosage form may comprise a pill, tablet, gelcap or other single dosage unit such as pre-measured powders or liquids. A filler or carrier material may be included to increase the volume of such composition. Suitable filler or carrier materials include, but are not limited to, various salts of sulfate, carbonate and silicate as well as talc, clay and the like. Filler or carrier materials for liquid compositions may be water or low molecular weight primary and secondary alcohols including polyols and diols. Examples of such alcohols include, but are not limited to, methanol, ethanol, propanol and isopropanol. The compositions may contain from about 5% to about 90% of such materials. Acidic fillers can be used to reduce pH. Alternatively, the cleaning additive may include activated peroxygen source defined below or the adjunct ingredients as fully defined below.

Applicants' cleaning compositions and cleaning additives require a catalytically effective amount of Applicants' organic catalyst. The required level of such catalyst may be achieved by the addition of one or more species of Applicants' organic catalyst. As a practical matter, and not by way of limitation, the compositions and cleaning processes herein can be adjusted to provide on the order of at least 0.001 ppm of Applicants' organic catalyst in the washing medium, and will preferably provide from about 0.001 ppm to about 500 ppm, more preferably from about 0.005 ppm to about 150 ppm, and most preferably from about 0.05 ppm to about 50 ppm, of the organic catalyst in the wash liquor. In order to obtain such levels in the wash liquor, typical compositions herein will comprise from about 0.0002% to about 5%, more preferably from about 0.001% to about 1.5%, of organic catalyst, by weight of the cleaning compositions.

When the Applicants' organic catalyst is employed in a granular composition, it may be desirable for the Applicants' organic catalyst to be in the form of an encapsulated particle to protect the Applicants' organic catalyst from moisture and/or other components of the granular composition during storage. In addition, encapsulation is also a means of controlling the availability of the Applicants' organic catalyst during the cleaning process and may enhance the bleaching performance of the Applicants' organic catalyst. In this regard, the Applicants' organic catalyst can be encapsulated with any encapsulating material known in the art.

The encapsulating material typically encapsulates at least part, preferably all, of the Applicants' organic catalyst. Typically, the encapsulating material is water-soluble and/or water-dispersible. The encapsulating material may have a glass transition temperature (Tg) of 0° C. or higher. Glass transition temperature is described in more detail in WO 97/11151, especially from page 6, line 25 to page 7, line 2. As such, WO 97/11151 is incorporated herein by reference.

The encapsulating material is preferably selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof. Preferably the encapsulating material is a carbohydrate, typically selected from the group consisting of monosaccharides, oligosaccharides, polysaccharides, and combinations thereof. Most preferably, the encapsulating material is a starch. Preferred starches are described in EP 0 922 499; U.S. Pat. No. 4,977,252; U.S. Pat. No. 5,354,559 and U.S. Pat. No. 5,935,826.

The encapsulating material may be a microsphere made from plastic such as thermoplastics, acrylonitrile, methacrylonitrile, polyacrylonitrile, polymethacrylonitrile and mixtures thereof; commercially available microspheres that can be used are those supplied by Expancel of Stockviksverken, Sweden under the trademark Expancel®, and those supplied by PQ Corp. of Valley Forge, Pa. U.S.A. under the tradename PM 6545, PM 6550, PM 7220, PM 7228, Extendospheres®, Luxsil®, Q-cel® and Sphericel®.

In addition to Applicants' organic catalysts, cleaning compositions must comprise an activated peroxygen source. Suitable ratios of moles of Applicants' organic catalyst to moles of activated peroxygen source include but are not limited to from about 1:1 to about 1:1000. Suitable activated peroxygen sources include, but are not limited to, preformed peracids, a hydrogen peroxide source in combination with a bleach activator, or a mixture thereof. Suitable preformed peracids include, but are not limited to, compounds selected from the group consisting of percarboxylic acids and salts, percarbonic acids and salts, perimidic acids and salts, peroxymonosulfuric acids and salts, and mixtures thereof. Suitable sources of hydrogen peroxide include, but are not limited to, compounds selected from the group consisting of perborate compounds, percarbonate compounds, perphosphate compounds and mixtures thereof.

Suitable bleach activators include, but are not limited to, tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters, perhydrolyzable imides and mixtures thereof.

When present, hydrogen peroxide sources will typically be at levels of from about 1%, preferably from about 5% to about 30%, preferably to about 20% by weight of the composition. If present, peracids or bleach activators will typically comprise from about 0.1%, preferably from about 0.5% to about 60%, more preferably from about 0.5% to about 40% by weight of the bleaching composition.

In addition to the disclosure above, suitable types and levels of activated peroxygen sources are found in U.S. Pat. Nos. 5,576,282, 6,306,812 B1 and 6,326,348 B1 that are incorporated by reference.

The cleaning compositions herein will preferably be formulated such that, during use in aqueous cleaning operations, the wash water will have a pH of between about 6.5 and about 11, preferably between about 7.5 and 10.5. Liquid dishwashing product formulations preferably have a pH between about 6.8 and about 9.0. Laundry products are typically at pH 9-11. Techniques for controlling pH at recommended usage levels include the use of buffers, alkalis, acids, etc., and are well known to those skilled in the art.

Adjunct Materials

While not essential for the purposes of the present invention, the non-limiting list of adjuncts illustrated hereinafter are suitable for use in the instant cleaning compositions and may be desirably incorporated in preferred embodiments of the invention, for example to assist or enhance cleaning performance, for treatment of the substrate to be cleaned, or to modify the aesthetics of the cleaning composition as is the case with perfumes, colorants, dyes or the like. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, dispersants, enzymes, and enzyme stabilizers, catalytic metal complexes, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

Surfactants—Preferably, the cleaning compositions according to the present invention comprise a surfactant or surfactant system wherein the surfactant can be selected from nonionic and/or anionic and/or cationic surfactants and/or ampholytic and/or zwitterionic and/or semi-polar nonionic surfactants.

The surfactant is typically present at a level of from about 0.1%, preferably about 1%, more preferably about 5% by weight of the cleaning compositions to about 99.9%, preferably about 80%, more preferably about 35%, most preferably about 30% by weight of the cleaning compositions.

Builders—The cleaning compositions of the present invention preferably comprise one or more detergent builders or builder systems. When present, the compositions will typically comprise at least about 1% builder, preferably from about 5%, more preferably from about 10% to about 80%, preferably to about 50%, more preferably to about 30% by weight, of detergent builder.

Builders include, but are not limited to, the alkali metal, ammonium and alkanolammonium salts of polyphosphates, alkali metal silicates, alkaline earth and alkali metal carbonates, aluminosilicate builders polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The cleaning compositions herein may also optionally contain one or more copper, iron and/or manganese chelating agents.

If utilized, these chelating agents will generally comprise from about 0.1% by weight of the cleaning compositions herein to about 15%, more preferably 3.0% by weight of the cleaning compositions herein.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

When present in the cleaning compositions herein, the dye transfer inhibiting agents are present at levels from about 0.0001%, more preferably about 0.01%, most preferably about 0.05% by weight of the cleaning compositions to about 10%, more preferably about 2%, most preferably about 1% by weight of the cleaning compositions.

Dispersants—The cleaning compositions of the present invention can also contain dispersants. Suitable water-soluble organic materials are the homo- or co-polymeric acids or their salts, in which the polycarboxylic acid comprises at least two carboxyl radicals separated from each other by not more than two carbon atoms.

Enzymes—The cleaning compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and known amylases, or mixtures thereof. A preferred combination is a cleaning composition having a cocktail of conventional applicable enzymes like protease, lipase, cutinase and/or cellulase in conjunction with amylase.

Enzyme Stabilizers—Enzymes for use in detergents can be stabilized by various techniques. The enzymes employed herein can be stabilized by the presence of water-soluble sources of calcium and/or magnesium ions in the finished compositions that provide such ions to the enzymes.

Catalytic Metal Comiplexes—Applicants' cleaning compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243 Bragg, issued Feb. 2, 1982.

If desired, the compositions herein can be catalyzed by means of a manganese compound. Such compounds and levels of use are well known in the art and include, for example, the manganese-based catalysts disclosed in U.S. Pat. No. 5,576,282 Miracle et al. Preferred examples of these catalysts include $Mn^{IV}_2(u-O)_3$(1,4,7-trimethyl-1,4,7-triazacyclononane) $_2$(PF$_6$)$_2$, Mn$^{III}_2$(u-O)$_1$(u-OAc)$_2$(1,4,7-trimethyl-1,4,7-triazacyclononane) $_2$(ClO$_4$)$_2$, Mn$^{IV}_4$(u-O)$_6$(1,4,7-triazacyclononane)$_4$(ClO$_4$)$_4$, Mn$^{III}$Mn$^{IV}_4$(u-O)$_1$(u-OAc)$_2$-(1,4,7-trimethyl-1,4,7-triazacyclononane)$_2$(ClO$_4$)$_3$, Mn$^{IV}$(1,4,7-trimethyl-1,4,7-triazacyclononane)-(OCH$_3$)$_3$(PF$_6$), and mixtures thereof.

Cobalt bleach catalysts useful herein are known, and are described, for example, in U.S. Pat. No. 5,597,936 Perkins et al., issued Jan. 28, 1997; U.S. Pat. No. 5,595,967 Miracle et al., Jan. 21, 1997. The most preferred cobalt catalyst useful herein are cobalt pentaamine acetate salts having the formula [Co(NH$_3$)$_5$OAc] Ty, wherein "OAc" represents an acetate moiety and "T$_y$" is an anion, and especially cobalt pentaamine acetate chloride, [Co(NH$_3$)$_5$OAc]Cl$_2$; as well as [Co(NH$_3$)$_5$OAc](OAc)$_2$; [Co(NH$_3$)$_5$OAc](PF$_6$)$_2$; [Co(NH$_3$)$_5$OAc](SO$_4$); [Co(NH$_3$)$_5$OAc](BF$_4$)$_2$; and [Co(NH$_3$)$_5$OAc](NO$_3$)$_2$ (herein "PAC"). Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the active MRL species in the aqueous washing medium, and will preferably provide from about 0.005 ppm to about 25 ppm, more preferably from about 0.05 ppm to about 10 ppm, and most preferably from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged. Such a ligand is non-limitingly illustrated below.

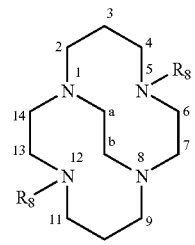

When each R$_8$ is ethyl, this ligand is named, 5,12-diethyl-1,5,8,12-tetraazabicyclo[6.6.2]hexadecane.

Transition-metal bleach catalysts of MRLs that are suitable for use in Applicants' cleaning compositions are non-limitingly illustrated by any of the following:

Dichloro-5,12-diethyl-1,5,8,12-tetraazabicyclo[6.6.2]hexadecane Manganese(II)
Diaquo-5,12-diethyl-1,5,8,12-tetraazabicyclo[6.6.2]hexadecane Manganese(II) Hexafluorophosphate
Aquo-hydroxy-5,12-diethyl-1,5,8,12-tetraazabicyclo[6.6.2]hexadecane Manganese(III) Hexafluorophosphate
Diaquo-5,12-diethyl-1,5,8,12-tetraazabicyclo[6.6.2]hexadecane Manganese(II) Tetrafluoroborate
Dichloro-5,12-diethyl-1,5,8,12-tetraazabicyclo[6.6.2]hexadecane Manganese(III) Hexafluorophosphate
Dichloro-5,12-di-n-butyl-1,5,8,12-tetraaza bicyclo[6.6.2] hexadecane Manganese(II)
Dichloro-5,12-dibenzyl-1,5,8,12-tetraazabicyclo[6.6.2] hexadecane Manganese(II)
Dichloro-5-n-butyl-12-methyl-1,5,8,12-tetraaza-bicyclo [6.6.2]hexadecane Manganese(II)
Dichloro-5-n-octyl-12-methyl-1,5,8,12-tetraaza-bicyclo [6.6.2]hexadecane Manganese(II)
Dichloro-5-n-butyl-12-methyl-1,5,8,12-tetraaza-bicyclo [6.6.2]hexadecane Manganese(II).

Suitable transition metal MRLs are readily prepared by known procedures, such as taught for example in WO 00/332601, and U.S. Pat. No. 6,225,464.

Processes of Making and Using of Applicants' Cleaning Composition

The cleaning compositions of the present invention can be formulated into any suitable form and prepared by any process chosen by the formulator, non-limiting examples of which are described in U.S. Pat. No. 5,879,584 Bianchetti et al., issued Mar. 9, 1999; U.S. Pat. No. 5,691,297 Nassano et al., issued Nov. 11, 1997; U.S. Pat. No. 5,574,005 Welch et al., issued Nov. 12, 1996; U.S. Pat. No. 5,569,645 Dinniwell et al., issued Oct. 29, 1996; U.S. Pat. No. 5,565,422 Del Greco et al., issued Oct. 15, 1996; U.S. Pat. No. 5,516,448 Capeci et al., issued May 14, 1996; U.S. Pat. No. 5,489,392 Capeci et al., issued Feb. 6, 1996; U.S. Pat. No. 5,486,303 Capeci et al., issued Jan. 23, 1996 all of which are incorporated herein by reference.

Method of Use

The present invention includes a method for cleaning a situs inter alia a surface or fabric. Such method includes the steps of contacting an embodiment of Applicants' cleaning composition, in neat form or diluted in a wash liquor, with at least a portion of a surface or fabric then rinsing such surface or fabric. Preferably the surface or fabric is subjected to a washing step prior to the aforementioned rinsing step. For purposes of the present invention, washing includes but is not limited to, scrubbing, and mechanical agitation. As will be appreciated by one skilled in the art, the cleaning compositions of the present invention are ideally suited for use in laundry applications. Accordingly, the present invention includes a method for laundering a fabric. The method comprises the steps of contacting a fabric to be laundered with a said cleaning laundry solution comprising at least one embodiment of Applicants cleaning composition, cleaning additive or mixture thereof. The fabric may comprise most any fabric capable of being laundered in normal consumer use conditions. The solution preferably has a pH of from about 8 to about 10.5. The compositions are preferably employed at concentrations of from about 500 ppm to about 15,000 ppm in solution. The water temperatures preferably range from about 5° C. to about 90° C. The water to fabric ratio is preferably from about 1:1 to about 30:1.

EXAMPLES

The following materials can be obtained from Aldrich, P.O. Box 2060, Milwaukee, Wis. 53201, USA: Epichlorohydrin, 2-ethylhexanol, stannic chloride, tetrahydrofuran, potassium tert-butoxide, 48% hydrobromic acid, methylene chloride, sodium bicarbonate, sodium sulfate, sulfur trioxide-dimethylformamide complex, diethyl ether, toluene, sulfur trioxide-trimethylamine complex, ethyl acetate, 1-octanol, 1-decanol, chlorosulfonic acid, 9-decene-1-ol, dioxane, 2,2,3,3,4,4,4-heptafluoro-1-butanol, [(6-hydroxyhexyl)oxy]trimethylsilane, and diethylene glycol mono hexylether. Synthesis routes for Examples 3 through 11 are depicted in Applicants' specification under the heading "Processes For Making Organic Catalyst"

Example 1

Preparation of (2-ethylhexyloxy)oxiran-2-ylmethane 2-ethylhexanol (20 g, 15 mmol) and stannic chloride (0.20 g, 1 mmol) are added to a flame dried, 1 L round bottomed flask equipped with an addition funnel charged with epichlorohydrin (15.62 g, 17 mmol). The reaction is kept under an argon gas atmosphere and warmed to 90° C. using an oil bath. Epichlorohydrin is dripped into the stirring solution over 1 hr., followed by stirring at 90° C. for 18 hr. The reaction is fitted with a vacuum distillation head and 1-chloro-3-(2-ethyl-hexyloxy)-propan-2-ol is distilled at a temperature range of from about 80° C. to about 85° C. under 0.2 mm Hg. The 1-chloro-3-(2-ethyl-hexyloxy)-propan-2-ol (5.0 g, 22 mmol) is dissolved in tetrahydrofuran (50 mL) and stirred and maintained at a temperature of from about 20° C. to about 25° C. under an argon atmosphere. Potassium tert-butoxide (2.52 g, 22 mmol) is added to the stirred solution and the suspension is stirred at from about 20° C. to about 25° C. for 18 h. to produce the glycidal ether.

Example 2

Preparation of 1-Bromo-3-(2-ethyl-hexyloxy)-propan-2-ol 2-ethylhexanol (20 g, 15 mmol) and stannic chloride (0.20 g, 1 mmol) are added to a flame dried, 1 L round bottomed flask equipped with an addition funnel charged with epichlorohydrin (15.62 g, 17 mmol). The reaction is kept under an argon gas atmosphere and warmed to 90° C. using an oil bath. Epichlorohydrin is dripped into the stirring solution over 1 hr. followed by stirring at 90° C. for 18 hr. Then reaction is fitted with a vacuum distillation head and 1-chloro-3-(2-ethyl-hexyloxy)-propan-2-ol is distilled under high vacuum. The 1-chloro-3-(2-ethyl-hexyloxy)-propan-2-ol (5.0 g, 22 mmol) is dissolved in tetrahydrofuran (50 mL) and stirred, while maintaining a temperature of from about 20° C. to about 25° C., under an argon atmosphere. Potassium tert-butoxide (2.52 g, 22 mmol) is added to the suspension and the temperature is maintained at from about 20° C. to about 25° C., with stirring, for 18 hr. to produce glycidal ether. Next, 48% hydrobromic acid (33 mmoles) is added to the reaction mixture that is maintained at a temperature of from about 20° C. to about 25° C. and stirred for 1 hr. The reaction is evaporated to dryness, the residue dissolved in methylene chloride (50 mL) and the organic solution washed with a 10% sodium bicarbonate solution (2×100 mL). The organic solution is dried with sodium sulfate, filtered and evaporated to dryness to afford a clear oil. This material is used without any further purification.

Example 3

Preparation of 4-[(2-ethylhexyloxymethyl]1,3,2-dioxathiolane-2,2-dione Via Synthesis Route 3 to 4

Sulfur trioxide-dimethylformamide complex ( 9.8 gm, 0.06399 mol.) and toluene (100 ml.) are added to a flame dried 3 neck round bottomed flask, equipped with an argon inlet, condenser, and a magnetic stir bar. The reaction is brought to reflux, and once at reflux, 2-ethylhexyloxy)oxiran-2-ylmethane (10.0 gm, 0.054 mol.) is added and the reaction refluxed for 45 minutes. The reaction is cooled to room temperature, diluted with diethyl ether (50 ml) and the resulting organic solution extracted with a saturated sodium bicarbonate solution. The organic phase is separated, dried with sodium sulfate, filtered, and the organic filtrate evaporated to dryness. The resulting 4-[(2-ethylhexyloxymethyl]-1,3,2-dioxathiolane-2,2-dione can be used without further purification.

Example 4

Preparation of Sulfuric acid mono-[2-(3,4-dihydro-isoquinolin-2-yl)-1-(2-ethyl-hexyloxymethyl)-ethyl] ester, Internal Salt Via Synthesis Route 4 to 5

Crude cyclic sulfate, toluene, and 3,4-dhydroisoquinoline (1 equivalent based on starting glycidal epoxide from cyclic sulfate reaction) is added to a 250 mL round bottomed flask. The reaction is maintained at a temperature of from about 20° C. to about 25° C. and stirred for 48 hours, upon which a solid/gel forms. The resulting solid/gel is isolated by filtration, to produce the desired product in >50% yield based on starting glycidal epoxide. Optionally, the product can be further purified by crystallization from an appropriate organic solvent.

Example 5

Preparation of Sulfuric acid mono-[2-(3,4-dihydro-isoquinolin-2-yl)-1-(2-ethyl-hexyloxymethyl)-ethyl] ester, Internal Salt Via Synthesis Route 2 to 6 to 5

1-Bromo-3-(2-ethyl-hexyloxy)-propan-2-ol, (19.25 gm., 0.072 moles), 3,4-Dihydroisoquinoline (9.45 gm., 0.072 moles) and dry acetonitrile (150 ML) is added to a 250 mL round bottomed flask. The reaction vessel is placed in a 50° C. oil bath and the reaction stirred for 48 hours under an atmosphere of argon gas. The reaction is then cooled to from about 20° C. to about 25° C., then sulfur trioxide-trimethylamine complex (10.0 gm., 0.072 moles) is added, and the reaction is brought to reflux. After stirring at reflux for 1 hour, the reaction is cooled to from about 20° C. to about 25° C. and then evaporated to dryness at reduced pressure, and the resulting residue is suspended in water (100 mL) at 90° C. for 15 minutes. The resulting solids are then isolated by filtration, and purified by crystallization from hot ethyl acetate to obtain the product as a white solid.

Example 6

Preparation of Sulfuric acid mono-[2-(3,4-dihydro-isoquinolin-2-yl)-1-(octyloxymethyl)-ethyl] ester, Internal Salt Via Synthesis Route 2 to 8 to 5

1-Bromo-3-(octyloxy)-propan-2-ol (1 equiv.), prepared according to Example 2 (except 1-octanol is substituted for 2-ethylhexanol), is treated with sulfur trioxide-DMF complex (1 equiv.) in stirring acetonitrile. The reactant mixture is stirred and maintained at temperature of from about 20° C. to about 25° C. for 2 hours followed by addition of sodium carbonate (3 equiv.). The resulting mixture is stirred and maintained at temperature of from about 20° C. to about 25° C. for 18 hours to obtain the Sulfuric acid mono-(1-bromomethyl-2-octyloxy-ethyl) ester, sodium salt. 3,4-dihydroisoquinoline (1 equiv.) is then added to the stirred mixture and the reaction is stirred at 50° C. for 24-48 hours to obtain the product.

Example 7

Preparation of Sulfuric acid mono-[2-(3,4-dihydro-isoquinolin-2-yl)-1-(decyloxymethyl)-ethyl] ester, Internal Salt Via Synthesis Route 3 to 7 to 6 to 5

2-Decyloxymethyl-oxirane (1 equiv.), prepared according to Example 1 (except 1-decanol is substituted for 2-ethylhexanol), is dissolved in acetonitrile and warmed to 70° C. Stannic chloride (0.1 equiv.) is added to the reaction, which is maintained at 70° C. with stirring for 24-48 hours to give the oxazolidine. The reaction is cooled to from about 20° C. to about 25° C. and chlorosulfonic acid (1 equiv.) is added to the reaction at a temperature of from about 20° C. to about 25° C. to yield the product, through sulfation of the putative intermediate 1-Decyloxy-3-(3,4-dihydro-isoquinolin-2-yl)-propan-2-ol.

Example 8

Preparation of Sulfuric acid mono-[2-(3,4-dihydro-isoquinolin-2-yl)-1-(9-deceneoxymethyl)-ethyl] ester, Internal Salt Via Synthesis Route 3 to 4 to 5

Glycidal ether (1 equiv.), prepared according to Example 1, (except 9-decene-1-ol is substituted for 2-ethylhexanol) is added drop wise to a stirred suspension of sulfur trioxide dimethylformamide complex (1 equiv.) in dioxane over 1 hour at 45° C. to give 4-Octyl-[1,3,2]dioxathiolane 2,2-dioxide. The dioxane is removed under reduced pressure and the residue dissolved in acetonitrile. Then 3,4-dihydroisoquinoline (1 equiv.) is added to the stirring solution and the reaction is maintained at temperature of from about 20° C. to about 25° C. with stirring for 24-48 hours. As the reaction mixture thickens, additional acetonitrile is added to aid in stirring. The product is collected as a solid, washed five times with acetone, and allowed to air dry.

Example 9

Preparation of Sulfuric acid mono-[2-(3,4-dihydro-isoquinolin-2-yl)-1-(2,2,3,3,4,4,4-heptafluorobutyloxymethyl)-ethyl] ester, Internal Salt Via Synthesis Route 3 to 4 to 5

Sulfuric acid mono-[2-(3,4-dihydro-isoquinolin-2-yl)-1-(2,2,3,3,4,4,4-heptafluorobutyloxymethyl)-ethyl] ester, internal salt, is prepared according to Example 8, except 9-decene-1-ol is replaced with 2,2,3,3,4,4,4-heptafluoro-1-butanol.

Example 10

Preparation of 3-{3-[1,1-bis(methylethyl)-2-methyl-1-silapropoxy]propoxy}-2-(2-3,4-dihydroisouinolylmethyl)propanesulfonic acid, Internal Salt Via Synthesis Route 3-{3-[1,3-dimethyl-2-(methylethyl)-2-silabutoxy]propoxy}-2-(2-3,4-dihydroisouinolylmethyl)propanesulfonic acid, internal salt, is prepared according to Example 8, except 9-decene-1-ol is replaced with 3-[1,1-bis(methylethyl)-2-methyl-1-silapropoxy]propane-1-ol (prepared according to the method of Lee et al., *Tetrahedron Letters*, 1996, No.21, pp. 3663-3666).

Example 11

Preparation of Sulfuric acid mono-{2-(3,4-dihydro-isoquinolin-2-yl)-1-[2-(2-hexyloxy-ethoxy)-ethoxymethyl]-ethyl} ester, Internal Salt Via Synthesis Route 3 to 4 to 5

Sulfuric acid mono-{2-(3,4-dihydro-isoquinolin-2-yl)-1-[2-(2-hexyloxy-ethoxy)-ethoxymethyl]-ethyl} ester, internal salt, is prepared according to Example 8, except 9-decene-1-ol is replaced with diethylene glycol mono hexylether.

Example 12

Bleaching detergent compositions having the form of granular laundry detergents are exemplified by the following formulations.

|  | A | B | C | D | E | F |
|---|---|---|---|---|---|---|
| Linear alkylbenzenesulfonate | 20 | 22 | 20 | 15 | 20 | 20 |
| $C_{12}$ Dimethylhydroxyethyl-ammonium chloride | 0.7 | 1 | 1 | 0.6 | 0.0 | 0.7 |
| AE3S | 0.9 | 0.0 | 0.9 | 0.0 | 0.0 | 0.9 |
| AE7 | 0.0 | 0.5 | 0.0 | 1 | 3 | 1 |
| sodium tripolyphosphate | 23 | 30 | 23 | 17 | 12 | 23 |
| Zeolite A | 0.0 | 0.0 | 0.0 | 0.0 | 10 | 0.0 |
| 1.6R Silicate | 7 | 7 | 7 | 7 | 7 | 7 |
| Sodium Carbonate | 15 | 14 | 15 | 18 | 15 | 15 |
| Polyacrylate MW 4500 | 1 | 0.0 | 1 | 1 | 1.5 | 1 |
| Carboxy Methyl Cellulose | 1 | 1 | 1 | 1 | 1 | 1 |
| Savinase 32.89 mg/g | 0.1 | 0.07 | 0.1 | 0.1 | 0.1 | 0.1 |
| Natalase 8.65 mg/g | 0.1 | 0.1 | 0.1 | 0.0 | 0.1 | 0.1 |
| Brightener 15 | 0.06 | 0.0 | 0.06 | 0.18 | 0.06 | 0.06 |
| Brightener 49 | 0.1 | 0.06 | 0.1 | 0.0 | 0.1 | 0.1 |
| Diethylenetriamine pentacetic acid | 0.6 | 0.3 | 0.6 | 0.25 | 0.6 | 0.6 |
| $MgSO_4$ | 1 | 1 | 1 | 0.5 | 1 | 1 |

-continued

|  | A | B | C | D | E | F |
|---|---|---|---|---|---|---|
| Sodium Percarbonate | 0.0 | 5.2 | 0.0 | 0.0 | 0.0 | 0.0 |
| Photobleach | 0.0030 | 0.0015 | 0.0015 | 0.0020 | 0.0045 | 0.0010 |
| Sodium Perborate Monohydrate | 4.4 | 0.0 | 3.85 | 2.09 | 0.78 | 3.63 |
| NOBS | 1.9 | 1.9 | 1.66 | 1.77 | 0.33 | 0.75 |
| TAED | 0.58 | 0.58 | 0.51 | 0.0 | 0.015 | 0.28 |
| Organic Catalyst * | 0.0185 | 0.0185 | 0.0162 | 0.0162 | 0.0111 | 0.0074 |
| Sulfate/Moisture | Balance to 100% | Balance to 100% | Balance to 100% | Balance to 100% | Balance to 100% | Balance to 100% |

* Sulfuric acid mono-[2-(3,4-dihydro-isoquinolin-2-yl)-1-(2-ethyl-hexyloxymethyl)-ethyl] ester, internal salt prepared according to Examples 4 or 5.

Any of the above compositions is used to launder fabrics at a concentration of 3500 ppm in water, 25° C., and a 25:1 water:cloth ratio. The typical pH is about 10 but can be can be adjusted by altering the proportion of acid to Na- salt form of alkylbenzenesulfonate.

Example 13

Bleaching detergent compositions having the form of granular laundry detergents are exemplified by the following formulations.

|  | A | B | C | D | E |
|---|---|---|---|---|---|
| Organic Catalyst * | 0.14 | 0.40 | 0.14 | 0.20 | 0.07 |
| Sodium Percarbonate | 5.30 | 0.00 | 0.00 | 4.00 | 0.00 |
| Sodium Perborate Monohydrate | 0.00 | 5.30 | 3.60 | 0.00 | 4.30 |
| Linear Alkylbenzenesulfonate | 12.00 | 0.00 | 12.00 | 0.00 | 21.00 |
| C45AE0.6S | 0.00 | 15.00 | 0.00 | 15.00 | 0.00 |
| $C_2$ Dimethylamine N-Oxide | 0.00 | 2.00 | 0.00 | 2.00 | 0.00 |
| $C_{12}$ Coco Amidopropyl Betaine | 1.50 | 0.00 | 1.50 | 0.00 | 0.00 |
| Palm N- Methyl Glucamide | 1.70 | 2.00 | 1.70 | 2.00 | 0.00 |
| $C_{12}$ Dimethylhydroxyethylammonium Chloride | 1.50 | 0.00 | 1.50 | 0.00 | 0.00 |
| AE23-6.5T | 2.50 | 3.50 | 2.50 | 3.50 | 1.00 |
| C25E3S | 4.00 | 0.00 | 4.00 | 0.00 | 0.00 |
| Conventional Activator (NOBS) | 0.00 | 0.00 | 0.60 | 0.00 | 0.00 |
| Conventional Activator (TAED) | 2.00 | 2.80 | 2.00 | 1.80 | 2.30 |
| Sodium Tripolyphosphate | 25.00 | 25.00 | 15.00 | 15.00 | 25.00 |
| Zeolite A | 0.00 | 0.00 | 0.00 | 0.00 | 0.00 |
| Acrylic Acid/Maleic Acid Copolymer | 0.00 | 0.00 | 0.00 | 0.00 | 1.00 |
| Polyacrylic Acid, partially neutralized | 3.00 | 3.00 | 3.00 | 3.00 | 0.00 |
| Soil Release Agent | 0.00 | 0.00 | 0.50 | 0.40 | 0.00 |
| Carboxymethylcellulose | 0.40 | 0.40 | 0.40 | 0.40 | 0.40 |
| Sodium Carbonate | 2.00 | 2.00 | 2.00 | 0.00 | 8.00 |
| Sodium Silicate | 3.00 | 3.00 | 3.00 | 3.00 | 6.00 |
| Sodium Bicarbonate | 5.00 | 5.00 | 5.00 | 5.00 | 5.00 |
| Savinase (4T) | 1.00 | 1.00 | 1.00 | 1.00 | 0.60 |
| Termamyl (60T) | 0.40 | 0.40 | 0.40 | 0.40 | 0.40 |
| Lipolase (100T) | 0.12 | 0.12 | 0.12 | 0.12 | 0.12 |
| Carezyme(5T) | 0.15 | 0.15 | 0.15 | 0.15 | 0.15 |
| Diethylenetriaminepenta(methylenephosphonic Acid) | 1.60 | 1.60 | 1.60 | 1.60 | 0.40 |
| Brightener | 0.20 | 0.20 | 0.20 | 0.05 | 0.20 |
| Sulfonated Zinc Phthalocyanine Photobleach | 0.50 | 0.00 | 0.25 | 0.00 | 0.00 |
| $MgSO_4$ | 2.20 | 2.20 | 2.20 | 2.20 | 0.64 |
| $Na_2SO_4$ | Balance to 100% | Balance to 100% | Balance to 100% | Balance to 100% | Balance to 100% |

* Sulfuric acid mono-[2-(3,4-dihydro-isoquinolin-2-yl)-1-(2-ethyl-hexyloxymethyl)-ethyl] ester, internal salt prepared according to Examples 4 or 5.

Any of the above compositions is used to launder fabrics at a concentration of 2500 ppm in water, 25° C., and a 15:1 water:cloth ratio. The typical pH is about 9.5 but can be can be adjusted by altering the proportion of acid to Na- salt form of alkylbenzenesulfonate.

Example 14

Bleaching detergent compositions having the form of granular laundry detergents are exemplified by the following formulations.

|  | A | B | C | D | E |
|---|---|---|---|---|---|
| Organic Catalyst * | 0.06 | 0.34 | 0.14 | 0.14 | 0.20 |
| Sodium Percarbonate | 5.30 | 0.00 | 0.00 | 0.00 | 0.00 |
| Sodium Perborate Monohydrate | 0.00 | 9.00 | 17.60 | 9.00 | 9.00 |
| Linear Alkylbenzenesulfonate | 21.00 | 12.00 | 0.00 | 12.00 | 12.00 |
| C45AE0.6S | 0.00 | 0.00 | 15.00 | 0.00 | 0.00 |
| $C_2$ Dimethylamine N-Oxide | 0.00 | 0.00 | 2.00 | 0.00 | 0.00 |
| $C_{12}$ Coco Amidopropyl Betaine | 0.00 | 1.50 | 0.00 | 1.50 | 1.50 |
| Palm N- Methyl Glucamide | 0.00 | 1.70 | 2.00 | 1.70 | 1.70 |
| $C_{12}$ Dimethylhydroxyethylammonium Chloride | 1.00 | 1.50 | 0.00 | 1.50 | 1.50 |
| AE23-6.5T | 0.00 | 2.50 | 3.50 | 2.50 | 2.50 |
| C25E3S | 0.00 | 4.00 | 0.00 | 4.00 | 4.00 |
| Conventional Activator (NOBS) | 0.00 | 0.00 | 0.00 | 1.00 | 0.00 |
| Conventional Activator (TAED) | 1.80 | 1.00 | 2.50 | 3.00 | 1.00 |
| Sodium Tripolyphosphate | 25.00 | 15.00 | 25.00 | 15.00 | 15.00 |
| Zeolite A | 0.00 | 0.00 | 0.00 | 0.00 | 0.00 |
| Acrylic Acid/Maleic Acid Copolymer | 0.00 | 0.00 | 0.00 | 0.00 | 0.00 |

-continued

|  | A | B | C | D | E |
|---|---|---|---|---|---|
| Polyacrylic Acid, partially neutralized | 0.00 | 3.00 | 3.00 | 3.00 | 3.00 |
| Soil Release Agent | 0.30 | 0.50 | 0.00 | 0.50 | 0.50 |
| Carboxymethylcellulose | 0.00 | 0.40 | 0.40 | 0.40 | 0.40 |
| Sodium Carbonate | 0.00 | 2.00 | 2.00 | 2.00 | 2.00 |
| Sodium Silicate | 6.00 | 3.00 | 3.00 | 3.00 | 3.00 |
| Sodium Bicarbonate | 2.00 | 5.00 | 5.00 | 5.00 | 5.00 |
| Savinase (4T) | 0.60 | 1.00 | 1.00 | 1.00 | 1.00 |
| Termamyl (60T) | 0.40 | 0.40 | 0.40 | 0.40 | 0.40 |
| Lipolase (100T) | 0.12 | 0.12 | 0.12 | 0.12 | 0.12 |
| Carezyme(5T) | 0.15 | 0.15 | 0.15 | 0.15 | 0.15 |
| Diethylenetriamine-penta(methylenephosphonic Acid) | 0.40 | 0.00 | 1.60 | 0.00 | 0.00 |
| Brightener | 0.20 | 0.30 | 0.20 | 0.30 | 0.30 |
| Sulfonated Zinc Phthalocyanine Photobleach | 0.25 | 0.00 | 0.00 | 0.00 | 0.00 |
| $MgSO_4$ | 0.64 | 0.00 | 2.20 | 0.00 | 0.00 |
| $Na_2SO_4$ | Balance to 100% | Balance to 100% | Balance to 100% | Balance to 100% | Balance to 100% |

* Sulfuric acid mono-[2-(3,4-dihydro-isoquinolin-2-yl)-1-(2-ethyl-hexyloxymethyl)-ethyl] ester, internal salt prepared according to Examples 4 or 5.

Any of the above compositions is used to launder fabrics at a concentration of 2500 ppm in water, 25° C., and a 15:1 water:cloth ratio. The typical pH is about 9.5 but can be can be adjusted by altering the proportion of acid to Na- salt form of alkylbenzenesulfonate.

Example 15

A bleaching detergent powder comprises the following ingredients:

| Component | Weight % |
|---|---|
| Organic Catalyst * | 0.07 |
| TAED | 2.0 |
| Sodium Perborate Tetrahydrate | 10 |
| $C_{12}$ linear alkyl benzene sulfonate | 8 |
| Phosphate (as sodium tripolyphosphate) | 9 |
| Sodium carbonate | 20 |
| Talc1 | 5 |
| Brightener, perfume | 0.3 |
| Sodium Chloride | 25 |
| Water | Balance to 100% |

* Sulfuric acid mono-[2-(3,4-dihydro-isoquinolin-2-yl)-1-(2-ethyl-hexyloxymethyl)-ethyl] ester, internal salt prepared according to Examples 4 or 5.

Example 16

A laundry bar suitable for hand-washing soiled fabrics is prepared by standard extrusion processes and comprises the following:

| Component | Weight % |
|---|---|
| Organic Catalyst * | 0.2 |
| TAED | 1.7 |
| NOBS | 0.2 |
| Sodium Perborate Tetrahydrate | 12 |
| $C_{12}$ linear alkyl benzene sulfonate | 30 |
| Phosphate (as sodium tripolyphosphate) | 10 |
| Sodium carbonate | 5 |

-continued

| Component | Weight % |
|---|---|
| Sodium pyrophosphate | 7 |
| Coconut monoethanolamide | 2 |
| Zeolite A (0.1-10 micron) | 5 |
| Carboxymethylcellulose | 0.2 |
| Polyacrylate (m.w. 1400) | 0.2 |
| Brightener, perfume | 0.2 |
| Protease | 0.3 |
| $CaSO_4$ | 1 |
| $MgSO_4$ | 1 |
| Water | 4 |
| Filler ** | Balance to 100% |

* Sulfuric acid mono-[2-(3,4-dihydro-isoquinolin-2-yl)-1-(2-ethyl-hexyloxymethyl)-ethyl] ester, internal salt prepared according to Examples 4 or 5.
** Can be selected from convenient materials such as $CaCO_3$, talc, clay, silicates, and the like. Acidic fillers can be used to reduce pH.

Example 17

A laundry detergent composition suitable for machine use is prepared by standard methods and comprises the following composition:

| | Weight % | |
|---|---|---|
| Component | Formula A | Formula B |
| Organic catalyst * | 0.82 | 1.0 |
| TAED | 7.20 | 10.0 |
| Sodium Perborate Tetrahydrate | 9.2 | 8.0 |
| Sodium Carbonate | 23.74 | 21.0 |
| Anionic surfactant | 14.80 | 12.0 |
| Alumino Silicate | 21.30 | 18.0 |
| Silicate | 1.85 | 0.00 |
| Diethylenetriaminepentacetic acid | 0.43 | 0.3 |
| Nonionic surfactant | 0.00 | 0.5 |
| Polyacrylic acid | 2.72 | 2.0 |
| Brightener | 0.23 | 0.3 |
| Polyethylene glycol solids | 1.05 | 0.00 |
| Sulfate | 8.21 | 17.0 |
| Perfume | 0.25 | 0.25 |
| Water | 7.72 | 6.7 |
| Processing aid | Balance to 100% | Balance to 100% |

* Sulfuric acid mono-[2-(3,4-dihydro-isoquinolin-2-yl)-1-(2-ethyl-hexyloxymethyl)-ethyl] ester, internal salt prepared according to Examples 4 or 5. The composition is used to launder fabrics at a concentration in solution of about 1000 ppm at a temperature of 20-40° C. and a water to fabric ratio of about 20:1.

Example 18

Method of Preparing a Starch Encapsulated Particle Comprising the Applicants' Organic Catalyst 151 g of the Applicants' organic catalyst according to any of Examples 1-11 above was slowly added to 7,550 g of an aqueous starch solution (33 wt % solids) in a high-shear mixer for 2 minutes. 190 g of sodium carbonate (which is dissolved in 498 g water) is added to this mixture, and the resulting mixture is mixed for 5 minutes in a high-shear mixer. This mixture is then spray dried using a Drytec Compact spray drier™ with an inlet temperature of 190° C. and an outlet temperature of 90° C., and with the exhaust fully open to form a starch encapsulated particle comprising 4.9 wt % Applicants' organic catalyst, 81 wt % starch, 6.2 wt % sodium carbonate and 7.9 wt % water.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process of making an organic catalyst comprising the steps of:
   a.) providing a substituted or unsubstituted halohydrin;
   b.) reacting said substituted or unsubstituted halohydrin with a substituted or unsubstituted 3,4-dihydroisoquinoline to form an alcohol salt;
   c.) sulfating said substituted alcohol salt to form an organic catalyst having the following formula:

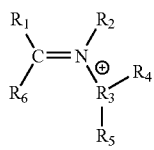

wherein: $R_1$ is a aryl group that can be substituted or unsubstituted;
$R_2$ is a substituted or unsubstituted alkyl;
$R_1$ and $R_2$ when taken together with the iminium form a six member ring
$R_3$ is a $C_1$ to $C_{20}$ substituted alkyl;
$R_4$ is the moiety $Q_t$-A
  wherein: Q is a branched or unbranched alkylene
  t=0 or 1 and
  A is an anionic group selected from the group consisting of $OSO_3^-$, $SO_3^-$, $CO_2^-$, $OCO_2^-$, $OPO_3^{2-}$, $OPO_3H^-$ and $OPO_2^-$;
$R_5$ is the moiety $-CR_{11}R_{12}-X-G_b-X_c-[(CR_9R_{10})_y-O]_k-R_8$
wherein: each X is independently selected from the group consisting of O, S, N—H, or N—$R_8$; and
  each $R_8$ is independently selected from the group consisting of alkyl, aryl and heteroaryl, said $R_8$ moieties being substituted or unsubstituted, and whether substituted or unsubstituted said $R_8$ moieties having less than 21 carbons;
  each G is independently selected from the group consisting of CO, $SO_2$, SO, PO and $PO_2$;
  $R_9$ and $R_{10}$ are independently selected from the group consisting of H and $C_1$-$C_4$ alkyl; and
  $R_{11}$ and $R_{12}$ are independently selected from the group consisting of H and alkyl, or when taken together may join to form a carbonyl; and
  b=0 or 1;
  c can=0 or 1, but c must=0 if b=0;
  y is an integer from 1 to 6;
  k is an integer from 0 to 20; and
$R_6$ H, or an alkyl aryl or heteroaryl moiety; said moieties being substituted or unsubstituted.

2. A process of making an organic catalyst according to claim 1 wherein the step of providing the halohydrin comprises reacting a substituted epoxide with a hydrogen halide.

3. A process of making an organic catalyst comprising the steps of:
   a.) providing a substituted epoxide;
   b.) reacting said substituted epoxide with a substituted or unsubstituted 3,4-dihydroisoquinoline in the presence of a Lewis acid catalyst to form a compound comprising an oxazolidine moiety;
   c.) reacting said compound comprising an oxazolidine moiety with a BrØnsted acid to form an alcohol salt;
   d.) sulfating said alcohol salt to form an organic catalyst having the following formula:

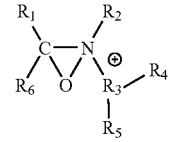

wherein: $R_1$ is a aryl group that can be substituted or unsubstituted;
$R_2$ is a substituted or unsubstituted alkyl;
$R_1$ and $R_2$ when taken together with the iminium form a six member ring
$R_3$ is a $C_1$ to $C_{20}$ substituted alkyl;
$R_4$ is the moiety $Q_t$-A
  wherein: Q is a branched or unbranched alkylene
  t=0 or 1 and
  A is an anionic group selected from the group consisting of $OSO_3^-$, $SO_3^-$, $CO_2^-$, $OCO_2^-$, $OPO_3^{2-}$, $OPO_3H^-$ and $OPO_2^-$;
$R_5$ is the moiety $-CR_{11}R_{12}-X-G_b-X_c-[(CR_9R_{10})_y-O]_k-R_8$
wherein: each X is independently selected from the group consisting of O, S, N—H, or N—$R_8$; and
  each $R_8$ is independently selected from the group consisting of alkyl, aryl and heteroaryl, said $R_8$ moieties being substituted or unsubstituted, and whether substituted or unsubstituted said $R_8$ moieties having less than 21 carbons;
  each G is independently selected from the group consisting of CO, $SO_2$, SO, PO and $PO_2$;
  $R_9$ and $R_{10}$ are independently selected from the group consisting of H and $C_1$-$C_4$alkyl; and
  $R_{11}$ and $R_{12}$ are independently selected from the group consisting of H and alkyl, or when taken together may join to form a carbonyl; and
  b=0 or 1;
  c can=0 or 1, but c must=0 if b=0;
  y is an integer from 1 to 6;
  k is an integer from 0 to 20; and
$R_6$ is H, or an alkyl, aryl or heteroaryl moiety; said moieties being substituted or unsubstituted.

4. A process of making an organic catalyst comprising the steps of:
   a.) providing a substituted epoxide;
   b.) reacting said substituted epoxide with $SO_3$, an $SO_3$ complex, or mixtures thereof to form a substituted cyclic sulfate;
   c.) reacting said substituted cyclic sulfate with a substituted or unsubstituted 3,4-dihydroisoquinoline to form an organic catalyst having the following formula:

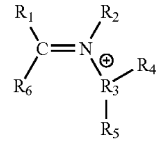

wherein: $R_1$ is a aryl group that can be substituted or unsubstituted;

$R_2$ is a substituted or unsubstituted alkyl;

$R_1$ and $R_2$ when taken together with the iminium form a six member ring $R_3$ is a $C_1$ to $C_{20}$ substituted alkyl;

$R_4$ is the moiety $Q_t$-A wherein: Q is a branched or unbranched alkylene t=0 or 1 and A is a anionic group selected from the group consisting of $OSO_3^-$, $SO_3^-$, $CO_2^-$, $OCO_2^-$, $OPO_3^{2-}$, $OPO_3H^-$ and $OPO_2^-$;

$R_5$ is the moiety —$CR_{11}R_{12}$—X-$G_b$-$X_c$—[$(CR_9R_{10})_y$—O]$_k$—$R_8$ wherein: each X is independently selected from the group consisting of O, S, N—H, or N—$R_8$; and each $R_8$ is independently selected from the group consisting of alkyl, aryl and heteroaryl, said $R_8$ moieties being substituted or unsubstituted, and whether substituted or unsubstituted said $R_8$ moieties having less than 21 carbons;

each G is independently selected from the group consisting of CO, $SO_2$, SO, PO and $PO_2$;

$R_9$ and $R_{10}$ are independently selected from the group consisting of H and $C_1$-$C_4$ alkyl; and $R_{11}$ and $R_{12}$ are independently selected from the group consisting of H and alkyl, or when taken together may join to form a carbonyl; and b=0 or 1;

c can=0 or 1, but c must=0 if b=0;

y is an integer from 1 to 6;

k is an integer from 0 to 20; and $R_6$ is H, or an alkyl, aryl or heteroaryl moiety; said moieties being substituted or unsubstituted.

* * * * *

UNITED STATES PATENT AND TRADEMARK OFFICE
CERTIFICATE OF CORRECTION

PATENT NO. : 7,507,700 B2
APPLICATION NO. : 11/437098
DATED : March 24, 2009
INVENTOR(S) : Miracle et al.

It is certified that error appears in the above-identified patent and that said Letters Patent is hereby corrected as shown below:

Title page Page 1
Item [56] Under Other Publications, line 5, delete "if" and insert -- of --.

Title page Page 2
Item [56] Under Other Publications, line 25, delete "Wittman" and insert -- Wittmann --.

Column 2
Lines 48 and 49, delete " $CH_2$, $-HC-(CH_2)_4-CH_2$, " and insert -- $CH_2$, $-HC-(CH_2)_4-CH_2$, --.

Column 3
Lines 3 and 4, delete " $-C=CHCH=CH-O.$ " and insert -- $-C=CHCH=CH-O.$ --.

Column 3
Lines 17-19, delete " and $-C=CHCH=CH-S.$ " and insert -- and $-C=CHCH=CH-S.$ --.

Column 3
Line 29, delete "-CAN," and insert -- -CN, --.

Column 15
Line 12, delete "18 hr." and insert -- 18 hr.. --.

Column 15
Line 36, delete "18 hr." and insert -- 18 hr.. --.

Column 15
Line 57, delete "[(2-ethylhexyloxymethyl]1,3,2-" and insert -- [(2-ethylhexyloxymethyl]-1,3,2- --.

UNITED STATES PATENT AND TRADEMARK OFFICE
CERTIFICATE OF CORRECTION

PATENT NO. : 7,507,700 B2
APPLICATION NO. : 11/437098
DATED : March 24, 2009
INVENTOR(S) : Miracle et al.

It is certified that error appears in the above-identified patent and that said Letters Patent is hereby corrected as shown below:

<u>Column 23</u>
Line 56, claim 1 delete "$R_6$ H," and insert -- $R_6$ is H, --.

Signed and Sealed this

Twenty-sixth Day of May, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,507,700 B2  Page 1 of 1
APPLICATION NO. : 11/437098
DATED : March 24, 2009
INVENTOR(S) : Miracle et al.

It is certified that error appears in the above-identified patent and that said Letters Patent is hereby corrected as shown below:

Column 24

Lines 6-13, delete " 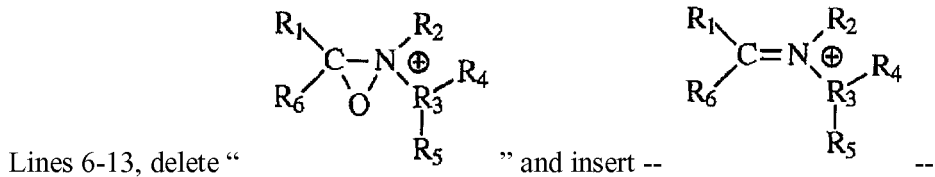 " and insert -- 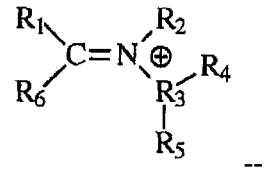 --

Signed and Sealed this
Twenty-third Day of August, 2011

David J. Kappos
*Director of the United States Patent and Trademark Office*